US010269602B1

(12) United States Patent
Lin et al.

(10) Patent No.: US 10,269,602 B1
(45) Date of Patent: Apr. 23, 2019

(54) WAFER WARPAGE INSPECTION SYSTEM AND METHOD USING THE SAME

(71) Applicant: TAIWAN SEMICONDUCTOR MANUFACTURING COMPANY LTD., Hsinchu (TW)

(72) Inventors: Wen-Yi Lin, New Taipei (TW); Po-Yao Lin, Hsinchu County (TW); Shin-Puu Jeng, Hsinchu (TW)

(73) Assignee: TAIWAN SEMICONDUCTOR MANUFACTURING COMPANY LTD., Hsinchu (TW)

( * ) Notice: Subject to any disclaimer, the term of this patent is extended or adjusted under 35 U.S.C. 154(b) by 0 days.

(21) Appl. No.: 15/928,768

(22) Filed: Mar. 22, 2018

Related U.S. Application Data

(60) Provisional application No. 62/591,501, filed on Nov. 28, 2017.

(51) Int. Cl.
| | |
|---|---|
| *H01L 21/67* | (2006.01) |
| *G01N 21/95* | (2006.01) |
| *G01B 11/16* | (2006.01) |
| *G01B 11/24* | (2006.01) |

(52) U.S. Cl.
CPC ........ *H01L 21/67288* (2013.01); *G01B 11/16* (2013.01); *G01B 11/24* (2013.01); *G01N 21/9501* (2013.01); *H01L 21/67103* (2013.01); *G01N 2201/0231* (2013.01)

(58) Field of Classification Search
CPC ........ H01L 21/67288; H01L 21/67103; G01B 11/16; G01B 11/24; G01N 21/9501; G01N 2201/0231
USPC ...................... 356/237.1–237.6, 239.1–239.8
See application file for complete search history.

(56) References Cited

U.S. PATENT DOCUMENTS

2012/0328194 A1* 12/2012 Iwanaga ................. G06T 5/009
382/168

* cited by examiner

*Primary Examiner* — Tri T Ton
(74) *Attorney, Agent, or Firm* — WPAT, P.C., Intellectual Property Attorneys; Anthony King

(57) ABSTRACT

The present disclosure provides a system for wafer warpage inspection including a heatable susceptor configured to heat a wafer according to a predetermined temperature profile. The system for wafer warpage inspection further includes a confocal imager array over the heatable susceptor configured to capture one or more warpage parameters of the wafer. Each confocal imager of the confocal imager array covers a predetermined field of view (FOV). The system for wafer warpage inspection further includes a first actuator permitting the confocal imager array to move in a plurality of directions. The system for wafer warpage inspection further includes a processing unit connected to the confocal imager array. The processing unit is configured to dynamically process the one or more warpage parameters captured during the heating of the wafer according to the predetermined temperature profile. Present disclosure also provides a method for wafer warpage inspection described herein.

20 Claims, 8 Drawing Sheets

WAFER WARPAGE INSPECTION SYSTEM AND METHOD USING THE SAME

PRIORITY CLAIM AND CROSS-REFERENCE

This application claims the benefit of prior-filed provisional application No. 62/591,501, filed Nov. 28, 2017.

BACKGROUND

A recent tendency in the field of semiconductor manufacturing is to reduce production costs by using larger wafers. The migration to a larger wafer size, while rewarding in an increased number of chips per wafer, also poses numerous technical challenges, such as maintenance of a uniform processing environment across a large wafer.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
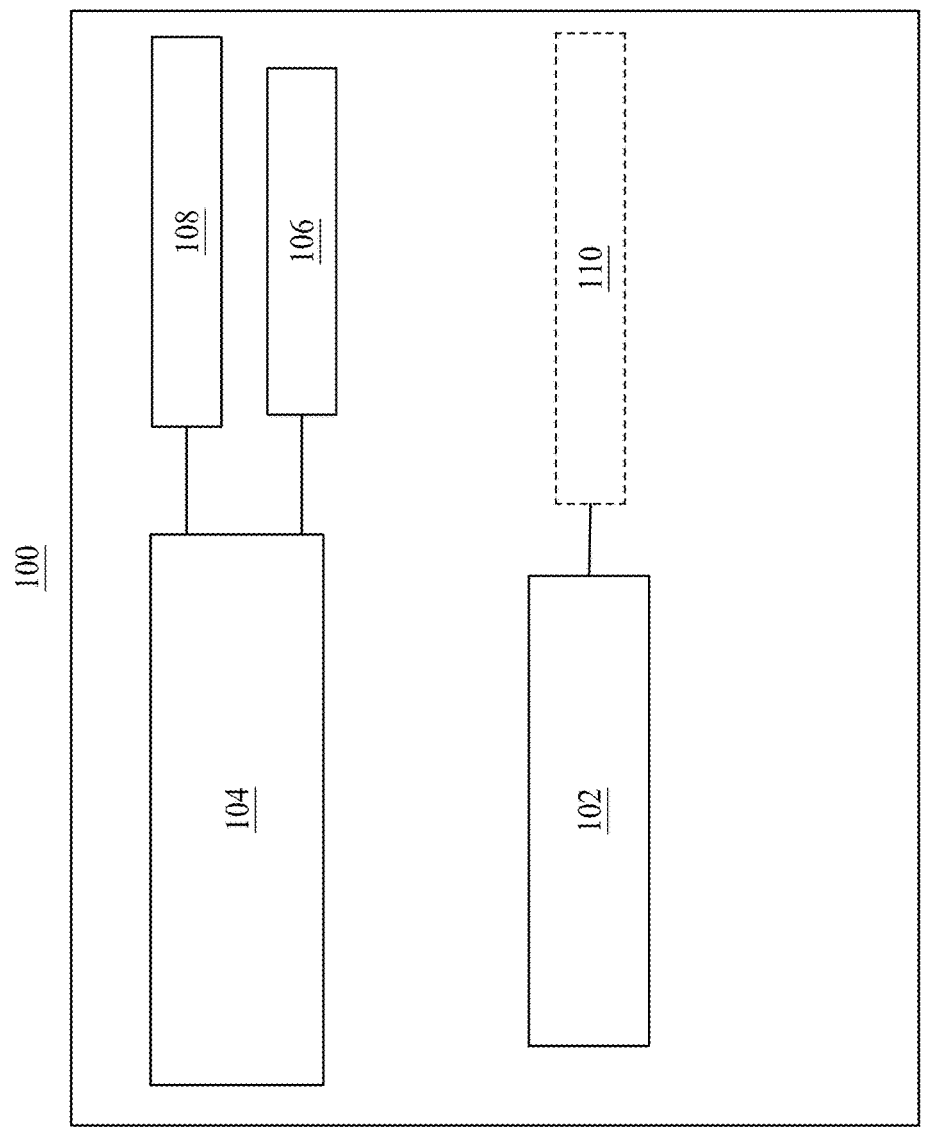
FIG. 1 is a block diagram illustrating a wafer warpage inspection system, in accordance with some embodiments of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Shadow Moiré is a well-known technique for wafer warpage inspection, but the need for sample preparation is time consuming and the limit of temperature raising rate may impact the accuracy of warpage information. For maintenance of a uniform processing environment across a large wafer, it is an object of the present disclosure to provide a system and a method allowing real-time and accurate wafer warpage inspection. The present disclosure doesn't need to do sample preparation and the temperature raising rate may closely represent the temperature variations in the production line. Besides, the confocal imager array used in the present disclosure can inspect the entire surface of the wafer more quickly.

Figure 2:
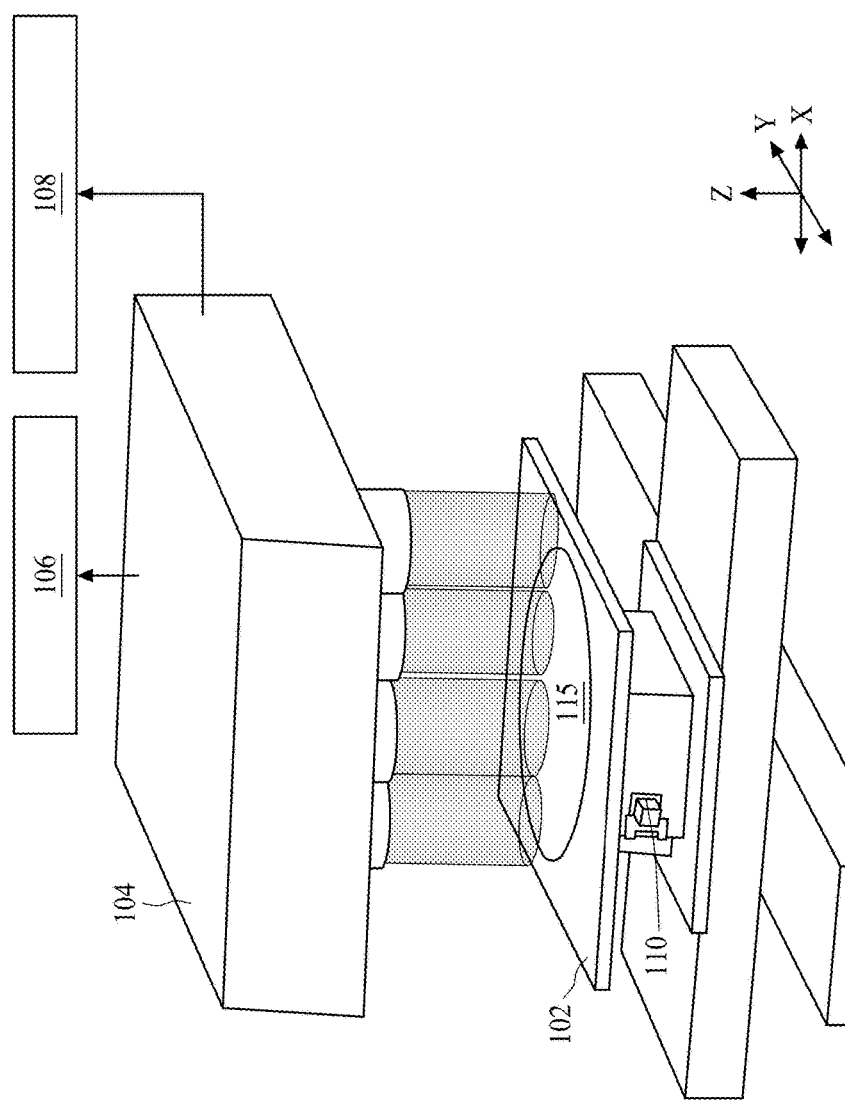
FIG. 2 is a schematic diagram illustrating a wafer warpage inspection system, in accordance with some embodiments of the present disclosure.
Figure 3:
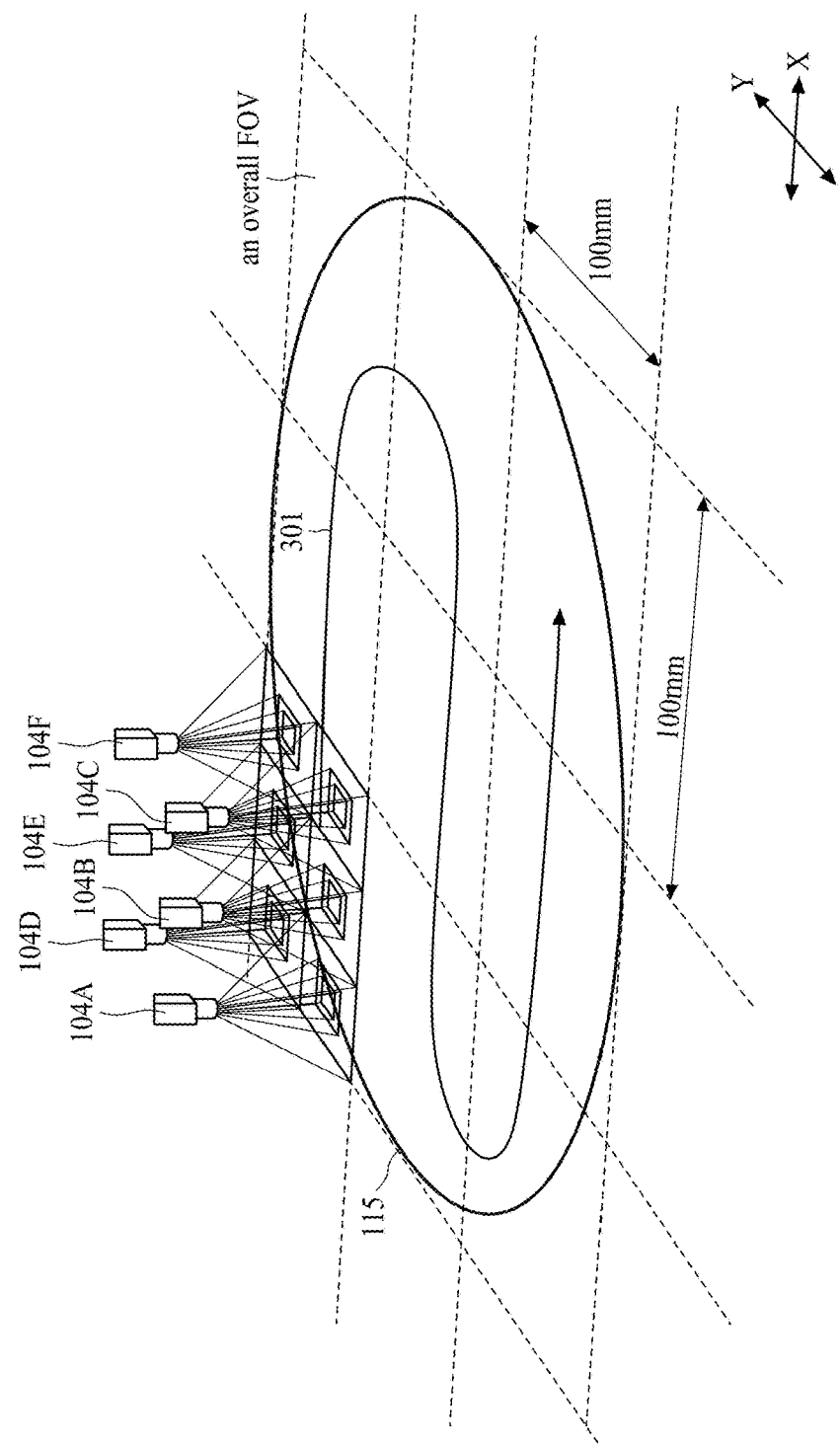
FIG. 3 is a partial schematic diagram illustrating a wafer warpage inspection system, in accordance with some embodiments of the present disclosure.

FIG. 1 is a block diagram illustrating a wafer warpage inspection system 100, in accordance with some embodiments of the present disclosure. FIG. 2 is a schematic diagram illustrating the wafer warpage inspection system 100 in FIG. 1, in accordance with some embodiments of the present disclosure. FIG. 3 is a partial schematic diagram illustrating a wafer warpage inspection system, in accordance with some embodiments of the present disclosure. The wafer warpage inspection system 100 will be further described according to one or more embodiments of the present disclosure.

Referring to FIGS. 1 and 2, the wafer warpage inspection system 100 includes a heatable susceptor 102, a confocal imager array 104, and a processing unit 108 connected to the confocal imager array 104. In some embodiments and hereinafter, the processing unit 108 can be a computer. In operation, the heatable susceptor 102 is configured to heat a wafer disposed thereon according to a predetermined temperature profile. For example, as shown in FIG. 2, a wafer 115 is held and heated on the heatable susceptor 102. In some embodiments of the present disclosure, the wafer 115 has a diameter equal to or greater than 300 mm, which is perceived prone to generate warpage during heating operations. It should be understood that the wafer 115 is a semiconductor substrate without solder balls and is just one kind of object that can be inspected with the wafer warpage inspection system 100 (referred to as unit under test in the present disclosure). In some embodiments of the present disclosure, in addition to the wafer 115, another kind of unit under test may be held on the heatable susceptor 102 to undergo a warpage inspection process, the examples of unit under test are a semiconductor package with solder balls on the surface, a semiconductor substrate coupled to a semiconductor package through solder balls, etc. The system and method of the present disclosure can be applied for any unit under test in order to inspect the warpage information thereof during heating operations.

In the current disclosure, a testing wafer can be loaded in the wafer warpage inspection system 100 and the system 100 obtains warpage information of the testing wafer during heating operations following a predetermined temperature profile. The warpage information obtained from the system 100 can then feedback to any stages on a production line producing product wafer by altering various parameters applied on the product wafer under substantial similar predetermined temperature profile as for the testing wafer.

The predetermined temperature profile is set up in the wafer warpage inspection system 100 according a temperature profile a product wafer undergoes in the production line. In some embodiments of the present disclosure, the predetermined temperature profile closely relates to the temperature profile used on the product wafer, so that the warpage parameters of the (testing) wafer 115 captured during the warpage inspection process may closely represent the warpage parameters of the product wafer to a sufficiently high extent. More details of the predetermined temperature profile will be provided below with reference to FIGS. 5A and 5B.

Still referring to FIGS. 1 and 2, the wafer 115 is held on the heatable susceptor 102, and the confocal imager array 104 is disposed over the wafer 115. In some embodiments of the present disclosure, the confocal imager array 104 is composed of a plurality of confocal imagers 104A to 104F, as shown in FIG. 3, and each confocal imager covers a predetermined field of view (FOV). The number of the confocal imagers per array 104 and the coverage of FOV per confocal imager shall be determined for the wafer warpage inspection system 100.

Referring to FIGS. 2 and 3, with regard to the number of the confocal imagers per array 104, it should be understood that although four confocal imagers and six confocal imagers are illustrated in FIG. 2 and FIG. 3, respectively, the confocal imager array 104 of current disclosure may include any number of the confocal imagers, as will be apparent to one of ordinary skill in the art. In some embodiments of the present disclosure, the number of the confocal imagers may be adjusted based on the required image-capturing resolution, the size of the unit under test, the cost, and so on. For example, if the number of the confocal imagers is enough for the overall FOV, the collective FOV of each of the confocal imagers, to cover up the entire surface of the wafer 115, then the movement of the confocal imager array 104 in the X-Y plane can be omitted. In this connection, the duration of the wafer warpage inspection can be shortened at the expense of the cost.

Referring to FIG. 3, with regard to the overall FOV of the confocal imager array 104, all of the confocal imagers 104A to 104F in the confocal imager array 104 collectively cover an overall FOV of about 100 mm times 100 mm. A single FOV is the area that each confocal imager can cover without any movement. The size of the single FOV can directly affect the image resolution for inspecting the wafer 115. It is should be noted that a smaller FOV may possess a greater resolution and vice versa. Besides, although a larger FOV results in a trade-off in the resolution, the larger FOV may be suitable for a larger area in order to obtain the warpage information on the same wafer more quickly. For example, as shown in FIG. 3, the overall FOV covers about one ninth of the entire surface of the wafer 115, so the confocal imager array 104 moves by nine steps to scan the entire surface of the wafer 115, as indicated by the scanning path 301. In the condition of a larger FOV, such as an overall FOV covering about one quarter of the entire surface, the confocal imager array 104 moves by four steps to scan the entire surface, which is lower in resolution but quicker. In some embodiments of the present disclosure, the resolution of each confocal imager is set to be greater than about 1 mm.

Returning to FIGS. 1 and 2, the wafer warpage inspection system 100 further includes a first actuator 106 permitting the confocal imager array 104 to move in a plurality of directions. In some embodiments of the present disclosure, the first actuator 106 permits the confocal imager array 104 to move along two perpendicular directions, such as the X and Y directions. For example, the confocal imager array 104 moves in an X-Y plane to scan the entire surface of the wafer 115 to capture one or more warpage parameters. Referring to FIG. 3, as mentioned above, the confocal imager array 104 may move by a certain number of steps in the X-Y plane to scan the entire surface of unit under test depending on the overall FOV. For example, the confocal imager array 104 moves by nine steps in the X-Y plane to scan the entire surface of the wafer 115, as indicated by the scanning path 301. In some embodiments of the present disclosure, the confocal imager array 104 moves in the X-Y plane while the heatable susceptor 102 heat the wafer 115 according to a predetermined temperature profile.

Returning to FIGS. 1 and 2, the processing unit 108 of the wafer warpage inspection system 100 connects to the confocal imager array 104. In operation, while the heatable susceptor 102 heats the wafer 115 according to a predetermined temperature profile, the processing unit 108 acquires one or more warpage parameters captured by the confocal imager array 104 and dynamically processes the one or more warpage parameters.

In some embodiments of the present disclosure, in addition to dynamically processing the one or more warpage parameters, the processing unit 108 further generates real time warpage information sequentially or synchronously. In some embodiments of the present disclosure, the real time warpage information may be outputted as a function of the predetermined temperature profile. In some embodiments of the present disclosure, by inputting the desired resolution of each of the confocal imagers to the processing unit 108, the processing unit 108 may determine the corresponding FOV of each of the confocal imagers.

Still referring to FIGS. 1 and 2, in some embodiments of the present disclosure, the wafer warpage inspection system 100 further includes a second actuator 110 permitting the heatable susceptor 102 to move in a direction perpendicular to a surface thereof to adjust a perpendicular distance between the wafer and the confocal imager array 104. For example, in FIG. 2, the heatable susceptor 102 can move along a Z direction. In some embodiments of the present disclosure, the heatable susceptor 102 moves in the Z direction while the heatable susceptor 102 heats the wafer 115 according to a predetermined temperature profile. It should be noted that, to avoid adverse impact on the gathering of warpage information of the wafer 115, the heatable susceptor 102 may only move perpendicularly with respect to the confocal imager array 104 during the capturing period (see FIG. 5A and FIG. 5B below). On the other hand, the confocal imager array 104 may move transversally with respect to the heatable susceptor 102 to cover the entire surface of the wafer 115 during the capturing period.

Figure 4:
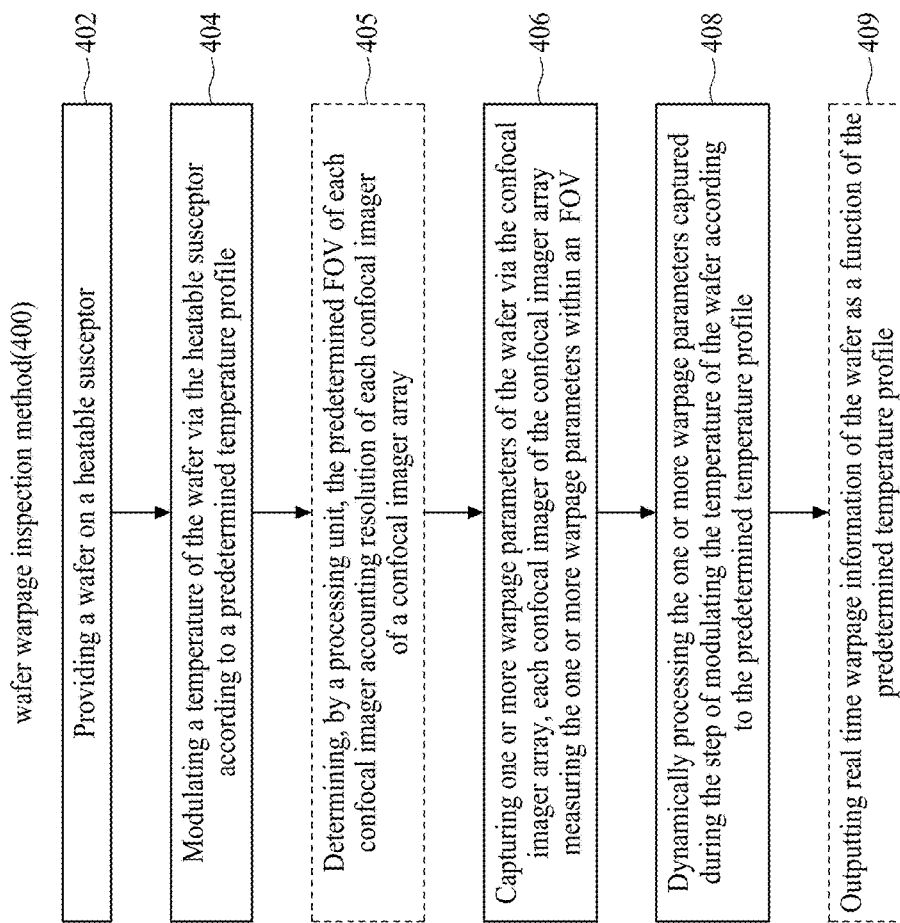
FIG. 4 is a flow chart of a wafer warpage inspection method, in accordance with some embodiments of the present disclosure.

Referring to FIG. 4, FIG. 4 is a flow chart of a wafer warpage inspection method 400, in accordance with some embodiments of the present disclosure. The wafer warpage inspection method 400 includes operation 402, providing a wafer on a heatable susceptor, operation 404, modulating a temperature of the wafer via the heatable susceptor according to a predetermined temperature profile, and operation 406, capturing one or more warpage parameters of the wafer via a confocal imager array, and each confocal imager of the confocal imager array measuring the one or more warpage parameters within an FOV. The wafer warpage inspection method 400 further includes operation 408, dynamically processing the one or more warpage parameters captured during the step of modulating the temperature of the wafer according to the predetermined temperature profile. It should be noted that the operations 402, 404, 406 in the wafer warpage inspection method 400 do not imply the steps are conducted sequentially, unless otherwise indicated. The wafer warpage inspection method 400 will be further described according to one or more embodiments of the present disclosure. Operations 405 and 409 are optional to the wafer warpage inspection method 400 and will be subsequently discussed in the present disclosure.

First, the wafer warpage inspection method 400 begins at operation 402, providing a wafer on a heatable susceptor. To facilitate understanding of the step 402, please see FIG. 2. As shown in FIG. 2, the wafer 115 is held on the heatable susceptor 102 with its surface parallel to the confocal imager array 104. As mentioned above, the wafer 115 can be another unit under test to be provided on the heatable susceptor to undergo a warpage inspection process.

Figure 5A:
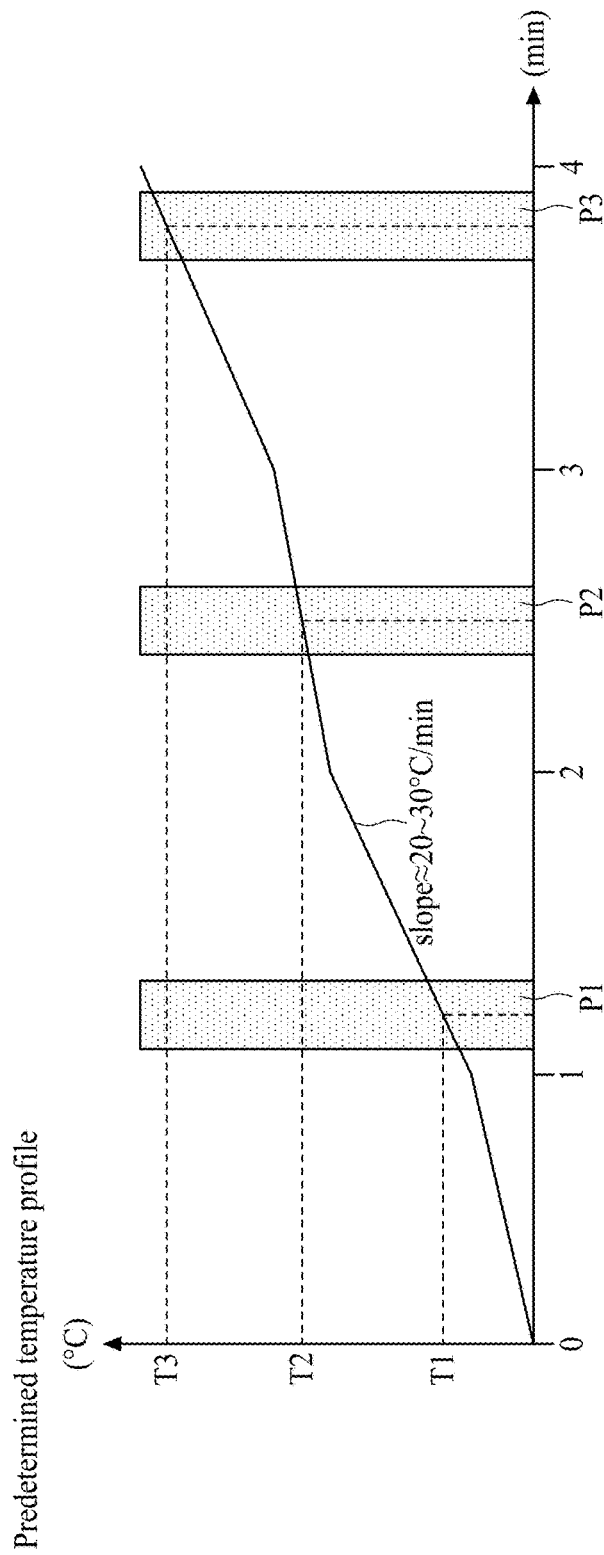
FIG. 5A shows a predetermined temperature profiles, in accordance with some embodiments of the present disclosure.
Figure 5B:
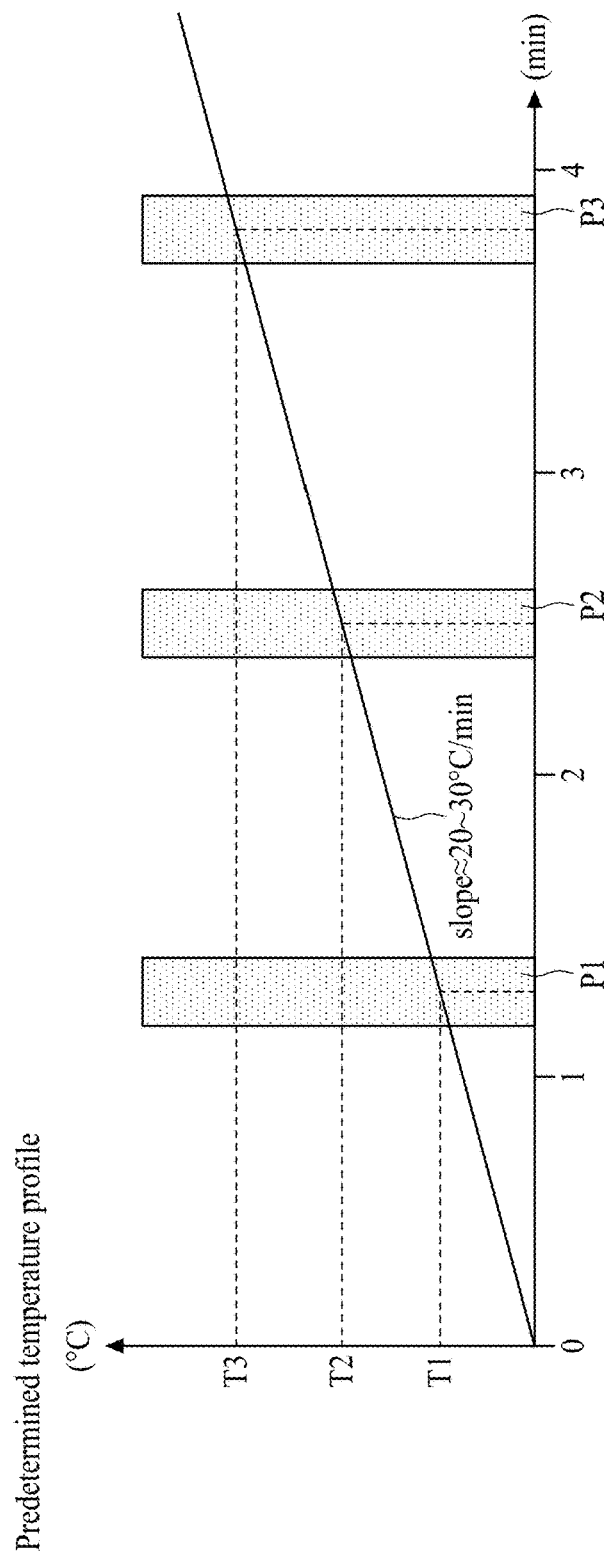
FIG. 5B shows a predetermined temperature profiles, in accordance with some embodiments of the present disclosure.

Following operation 402, the wafer warpage inspection method 400 proceeds to the operation 404, modulating a temperature of the wafer via the heatable susceptor according to a predetermined temperature profile. To facilitate understanding of the step 404, please see FIGS. 5A and 5B. FIGS. 5A and 5B are diagrams showing predetermined temperature profiles, in accordance with some embodiments of the present disclosure.

Referring to FIG. 5A, the diagram of FIG. 5A shows a piecewise linear profile, wherein the temperature is a function of time. The piecewise linear profile includes a plurality of different slopes ranging from about 20 degrees Celsius increment per minute (° C./min) to about 30 degrees Celsius increment per minute. In some embodiments of the present disclosure, the piecewise linear profile includes slopes with at least 20 degrees Celsius increment per minute. For example, please see FIG. 5B, the diagram of FIG. 5B shows a linear profile with a single slope, which can range from about 20 degrees Celsius increment per minute (° C./min) to about 30 degrees Celsius increment per minute. It should be easily realized by those skilled in the art that in operation 404, the temperature of the wafer is raised by a rate faster than those used in conventional methods.

The predetermined temperature profiles in FIGS. 5A and 5B are illustrated for explanation only, and the disclosure is not limited thereto. Furthermore, the predetermined temperature profile may closely relate to the real temperature profile applied on a product wafer in a production line.

Next, while the temperature of the wafer is being modulated according to the predetermined temperature profile, the wafer warpage inspection method 400 proceeds to the operation 406, capturing one or more warpage parameters of the wafer via a confocal imager array. It is should be understood that the duration of the temperature modulation may last during the entire course of the wafer warpage inspection method 400. However, several capturing periods are set when several target temperatures are reached. To facilitate understanding of the operation 406, please see FIGS. 5A and 5B.

Referring to FIGS. 5A and 5B, a plurality of target temperatures T1, T2, and T3 are set in the predetermined temperature profiles. The plurality of target temperatures T1, T2, and T3 are the temperatures under which the warpage parameters of the wafer desired to be captured. In FIGS. 5A and 5B, operation 406, or warpage parameters capturing, is conducted during a plurality of capturing periods P1, P2, and P3 indicated with shaded columns. The plurality of capturing periods P1, P2, and P3 are confocal imager array capturing periods set around the plurality of target temperatures T1, T2, and T3, say between positive and negative 2.5 degrees Celsius with respect to T1, T2, and T3. In some embodiments of the present disclosure, each of the plurality of capturing periods P1, P2, and P3 lasts 5 to 7 seconds.

As mentioned above, the operations in the wafer warpage inspection method 400 are not necessarily conducted sequentially. In some embodiments of the present disclosure, some operations may be performed synchronically. For example, in FIGS. 5A and 5B, operation 404 is performed throughout the entire wafer warpage inspection method 400, and operation 406 is performed during the plurality of capturing periods P1, P2, and P3.

For further understanding of operation 406, please see FIG. 3. In some embodiments of the present disclosure, operation 406 further includes transversally translating the confocal imager array 104 over the heatable susceptor during each of the plurality of capturing periods P1. P2, and P3. For example, the transversal translation of the confocal imager array 104 may be realized by the first actuator 106. The confocal imager array 104 moves in the X-Y plane, as shown in FIG. 3. In some embodiments of the present disclosure, the confocal imager array 104 moves by multiple steps in the X-Y plane to cover the entire surface of the wafer 115 during each of the plurality of capturing periods P1, P2, and P3, as indicated by the scanning path 301 in FIG. 3.

For further understanding of operation 406, please see FIG. 2. In some embodiments of the present disclosure, operation 406 further includes vertically moving the heatable susceptor 102 during the plurality of capturing periods P1, P2, and P3. For example, the vertical movement of the heatable susceptor may be realized by the second actuator 110. The heatable susceptor 102 moves in the Z direction to adjust the perpendicular distance between the wafer 115 and the confocal imager array 104. In some embodiments of the present disclosure, in operation 406, the heatable susceptor 102 may move along the Z direction after every transversal translation of the confocal imager array is completed, thereby the warpage information on the vertical direction can be obtained in such intermediate step without transversal movement. In some embodiments, the heatable susceptor 102 may move along the Z direction synchronously with every transversal translation of the confocal imager array.

Subsequently, the wafer warpage inspection method 400 proceeds to the operation 408, dynamically processing the one or more warpage parameters captured during operation of modulating the temperature of the wafer according to the predetermined temperature profile. It should be understood that the operation 408 may be conducted sequentially or synchronously with operation 406. In some embodiments of the present disclosure, operation 408 may be realized with the processing unit 108. For example, please see FIG. 2, in operation 408, the processing unit 108 acquires the one or more warpage parameters captured by the confocal imager array 104 and dynamically processes the one or more warpage parameters. In some embodiments of the present disclosure, the processing unit 108 further generates real time warpage information. In some embodiments of the present disclosure, the real time warpage information may be outputted as a function of the predetermined temperature profile, as indicated as an optional operation 409 in FIG. 4.

Returning to FIG. 4, in operation 406, each confocal imager of the confocal imager array 104 measures the one or more warpage parameters within a predetermined FOV. In some embodiments of the present disclosure, the wafer warpage inspection method 400 further includes an operation 405, determining the FOV of each confocal imager accounting resolution of each confocal imager of the confocal imager array by a processing unit 108. For example, a user may input desired resolution of each confocal imager into the processing unit 108, and the processing unit 108 determines the FOV of each confocal imager corresponding to the desired resolution. It is should be understood that although operation 405 is illustrated between operations 404 and 406, operation 405 may be performed automatically at any time throughout the wafer warpage inspection method 400.

Figure 6:
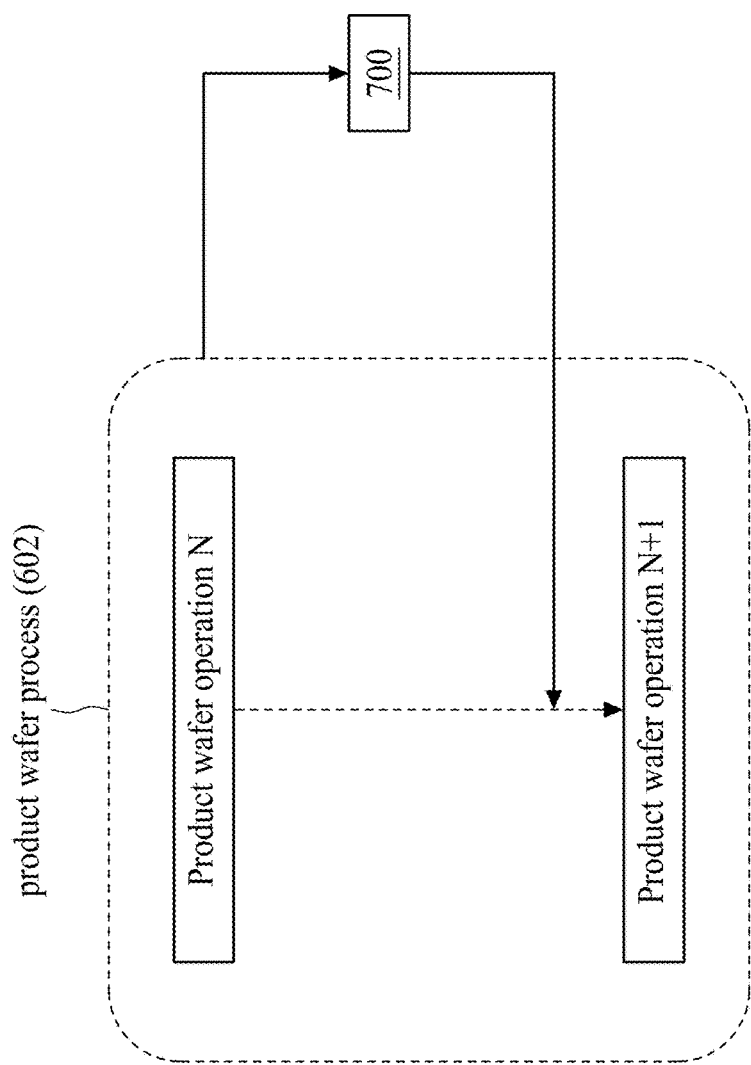
FIG. 6 shows a method for optimizing warpage-sensitive processing parameters to a product wafer, in accordance with some embodiments of the present disclosure.

Referring to FIG. 6, FIG. 6 is an illustration showing a method for optimizing warpage-sensitive processing parameters to a product wafer, in accordance with some embodiments of the present disclosure. As previously discussed, a testing wafer can be loaded in the wafer warpage inspection system 100 to perform a testing wafer process 700. After the system 100 obtaining warpage information of the testing wafer during heating operations, the warpage information can then feedback to any stages of a product wafer process 602 by altering various parameters applied on the product wafer under substantial similar heating operations as for the testing wafer. As shown in FIG. 6, product wafer process 602 includes a plurality of product wafer operations 0, 1, 2, . . . . N, N+1, etc., wherein N is a positive integer. After product wafer operation N and before entering product wafer operation N+1 associated with heating operation, a testing wafer process 700 is initiated and the warpage parameters are captured as previously described in wafer warpage inspection method 400. Compared to wafer warpage inspection method 400, the testing wafer process 700 further includes optimizing warpage-sensitive processing parameters to the product wafer according to the corresponding warpage information of the testing wafer. For instance, the warpage information gathered is then feedback to the product wafer process 602 to optimize warpage-sensitive processing parameters implemented in the product wafer process 602.

Figure 7:
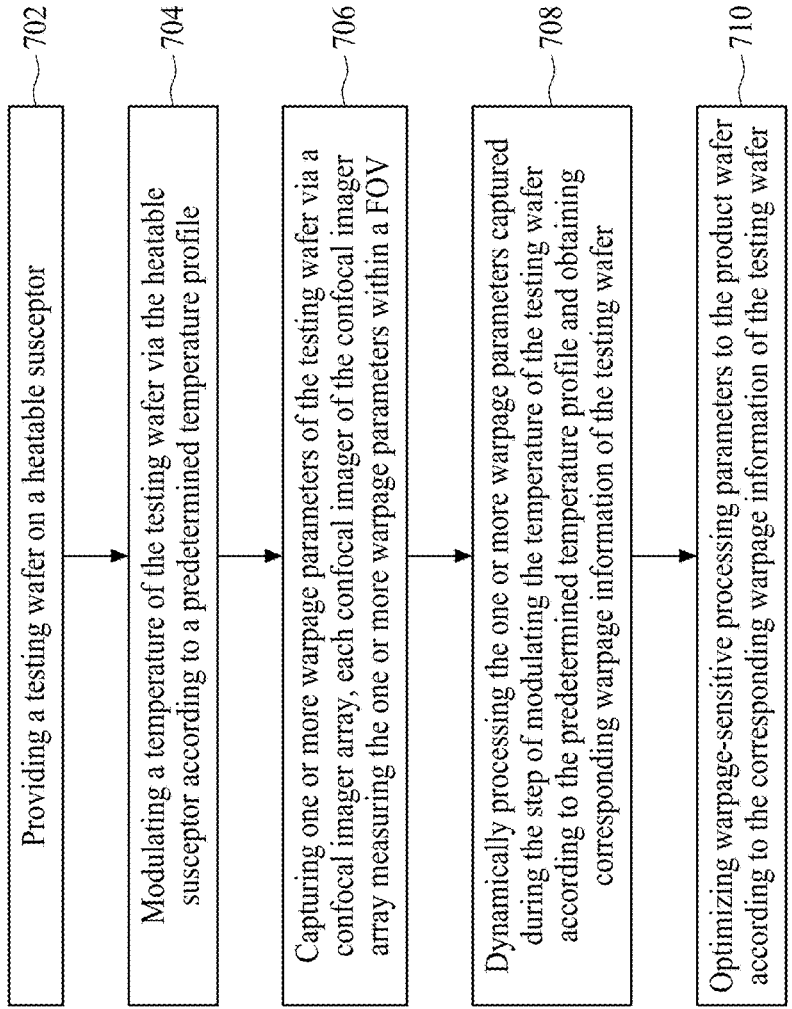
FIG. 7 is a flow chart of the testing wafer process in FIG. 6, in accordance with some embodiments of the present disclosure.

Referring to FIG. 7, FIG. 7 is a flow chart of the testing wafer process 700 in FIG. 6, in accordance with some embodiments of the present disclosure. The testing wafer process 700 includes operation 702, providing a testing wafer on a heatable susceptor, operation 704, modulating a temperature of the testing wafer via the heatable susceptor according to a predetermined temperature profile operation 706, capturing one or more warpage parameters of the testing wafer via a confocal imager array. Each confocal imager of the confocal imager array measuring the one or more warpage parameters within a predetermined FOV. The testing wafer process 700 further includes operation 708, dynamically processing the one or more warpage parameters captured during the step of modulating the temperature of the testing wafer according to the predetermined temperature profile and obtaining corresponding warpage information of the testing wafer and operation 710, optimizing warpage-sensitive processing parameters to the product wafer according to the corresponding warpage information of the testing wafer.

Still referring to FIG. 7, since operations 702 to 706 for testing wafer are similar to operations 402 to 406 for wafer described above in relation to FIG. 4, such similar details are omitted in the interest of brevity, and the differences are provided. In the testing wafer process 700, the predetermined temperature profile in operation 704 may closely relate to the temperature profile used in the product wafer process 602. Besides, in the testing wafer process 700, the corresponding warpage information of the testing wafer is obtained in operation 708 and is feedback to the product wafer process 602 in operation 710. Therefore, the warpage-sensitive processing parameters of the product wafer can be optimized according to the corresponding warpage information of the testing wafer.

Some embodiments provide a system for wafer warpage inspection including a heatable susceptor configured to heat a wafer according to a predetermined temperature profile. The system for wafer warpage inspection further includes a confocal imager array over the heatable susceptor. The confocal imager array is configured to capture one or more warpage parameters of the wafer. Each confocal imager of the confocal imager array covers a field of view (FOV). The system for wafer warpage inspection further includes a first actuator permitting the confocal imager array to move in a plurality of directions. The system for wafer warpage inspection further includes a processing unit connected to the confocal imager array. The processing unit is configured to dynamically process the one or more warpage parameters captured during the heating of the wafer according to the predetermined temperature profile.

Some embodiments provide a method for wafer warpage inspection, including (1) providing a wafer on a heatable susceptor; (2) modulating a temperature of the wafer via the heatable susceptor according to a predetermined temperature profile; (3) capturing one or more warpage parameters of the wafer via a confocal imager array, each confocal imager of the confocal imager array measuring the one or more warpage parameters within a field of view (FOV); and (4) dynamically processing the one or more warpage parameters captured during the step of modulating the temperature of the wafer according to the predetermined temperature profile.

Some embodiments provide a method for optimizing warpage-sensitive processing parameters to a product wafer, including (1) providing a testing wafer on a heatable susceptor; (2) modulating a temperature of the testing wafer via the heatable susceptor according to a predetermined temperature profile; (3) capturing one or more warpage parameters of the testing wafer via a confocal imager array, each confocal imager of the confocal imager array measuring the one or more warpage parameters within a field of view (FOV); (4) dynamically processing the one or more warpage parameters captured during the step of modulating the temperature of the testing wafer according to the predetermined temperature profile and obtaining corresponding warpage information of the testing wafer; and (5) optimizing warpage-sensitive processing parameters to the product wafer according to the corresponding warpage information of the testing wafer.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A system for wafer warpage inspection, comprising:
   a heatable susceptor configured to heat a wafer according to a predetermined temperature profile;
   a confocal imager array over the heatable susceptor, configured to capture one or more warpage parameters of the wafer, wherein each confocal imager of the confocal imager array covers a predetermined field of view;
   a first actuator permitting the confocal imager array to move in a plurality of directions; and
   a computer connected to the confocal imager array, configured to dynamically process the one or more warpage parameters captured during the heating of the wafer according to the predetermined temperature profile.

2. The system of claim 1, wherein the first actuator permits the confocal imager array to move along two perpendicular directions.

3. The system of claim 1, wherein all of the confocal imagers in the confocal imager array collectively cover an overall FOV of about 100 mm times 100 mm.

4. The system of claim 1, wherein the computer dynamically processes the one or more warpage parameters and generates real time warpage information of the wafer.

5. The system of claim 3, wherein resolution of each confocal imager is greater than about 1 mm.

6. The system of claim 1, wherein the heatable susceptor comprises:
   a second actuator permitting the heatable susceptor to move in a direction perpendicular to a surface thereof.

7. A method for wafer warpage inspection, comprising:
   providing a wafer on a heatable susceptor;
   modulating a temperature of the wafer via the heatable susceptor according to a predetermined temperature profile;
   capturing one or more warpage parameters of the wafer via a confocal imager array, each confocal imager of the confocal imager array measuring the one or more warpage parameters within a field of view (FOV); and
   dynamically processing the one or more warpage parameters captured during the modulating the temperature of the wafer according to the predetermined temperature profile.

8. The method of claim 7, wherein the predetermined temperature profile comprises a piecewise linear profile.

9. The method of claim 8, wherein the modulating the temperature of the wafer comprises raising more than 20 degrees Celsius per minute.

10. The method of claim 7, wherein the capturing one or more warpage parameters of the wafer is conducted during a plurality of capturing periods along the predetermined temperature profile.

11. The method of claim 10, further comprising:
    transversally translating the confocal imager array over the heatable susceptor during the plurality of capturing periods.

12. The method of claim 11, further comprising:
    vertically moving the heatable susceptor during the plurality of capturing periods.

13. The method of claim 7, further comprising:
    outputting real time warpage information of the wafer as a function of the predetermined temperature profile.

14. The method of claim 7, further comprising:
    determining, by a processing unit, the FOV of each confocal imager accounting resolution of each confocal imager of the confocal imager array.

15. A method for optimizing warpage-sensitive processing parameters to a product wafer, comprising:
    providing a testing wafer on a heatable susceptor;
    modulating a temperature of the testing wafer via the heatable susceptor according to a predetermined temperature profile;
    capturing one or more warpage parameters of the testing wafer via a confocal imager array, each confocal imager of the confocal imager array measuring the one or more warpage parameters within a field of view (FOV);
    dynamically processing the one or more warpage parameters captured during the modulating the temperature of the testing wafer according to the predetermined temperature profile and obtaining corresponding warpage information of the testing wafer; and
    optimizing warpage-sensitive processing parameters to the product wafer according to the corresponding warpage information of the testing wafer.

16. The method of claim 15, wherein the predetermined temperature profile comprises a piecewise linear profile.

17. The method of claim 15, wherein the capturing one or more warpage parameters of the testing wafer is conducted during a plurality of capturing periods along the predetermined temperature profile.

18. The method of claim 17, further comprising:
    transversally translating the confocal imager array over the heatable susceptor during the plurality of capturing periods.

19. The method of claim 18, further comprising vertically moving the heatable susceptor during the plurality of capturing periods.

20. The method of claim 15, further comprising:
    outputting real time warpage information of the testing wafer as a function of the predetermined temperature profile.

* * * * *